US012023322B2

(12) United States Patent
Pedersen et al.

(10) Patent No.: US 12,023,322 B2
(45) Date of Patent: Jul. 2, 2024

(54) RUFINAMIDE FOR USE IN THE TREATMENT OF MYOTONIA

(71) Applicant: AARHUS UNIVERSITET, Aarhus (DK)

(72) Inventors: Thomas Holm Pedersen, Risskov (DK); Martin Brandhøj Skov, Aarhus (DK)

(73) Assignee: AARHUS UNIVERSITET, Aarhus C (DK)

( * ) Notice: Subject to any disclaimer, the term of this patent is extended or adjusted under 35 U.S.C. 154(b) by 0 days.

(21) Appl. No.: 16/061,293

(22) PCT Filed: Dec. 9, 2016

(86) PCT No.: PCT/DK2016/050424
§ 371 (c)(1),
(2) Date: Jun. 11, 2018

(87) PCT Pub. No.: WO2017/097311
PCT Pub. Date: Jun. 15, 2017

(65) Prior Publication Data
US 2018/0369207 A1 Dec. 27, 2018

(30) Foreign Application Priority Data
Dec. 11, 2015 (EP) .................................. 15199512

(51) Int. Cl.
*A61K 31/4192* (2006.01)
*A61K 31/00* (2006.01)
*A61K 31/165* (2006.01)
*A61K 31/53* (2006.01)
*A61P 21/02* (2006.01)

(52) U.S. Cl.
CPC .......... *A61K 31/4192* (2013.01); *A61K 31/00* (2013.01); *A61K 31/165* (2013.01); *A61K 31/53* (2013.01); *A61P 21/02* (2018.01); *A61K 2300/00* (2013.01)

(58) Field of Classification Search
CPC .............. C07D 249/04; C07D 253/075; A61K 31/4192; A61K 31/53; A61P 21/02
USPC .......................................... 514/359; 548/255
See application file for complete search history.

(56) References Cited

U.S. PATENT DOCUMENTS 4,789,680 A * 12/1988 Meier ...................... C07C 33/46
514/359
2011/0207718 A1 8/2011 Bird

FOREIGN PATENT DOCUMENTS

| CN | 101636180 A | 1/2010 |
| EP | 0 199 262 A2 | 10/1986 |
| JP | 2009-541397 A | 11/2009 |
| JP | 2011-529923 A | 12/2011 |
| WO | 2008/000513 A2 | 1/2008 |
| WO | 2014/120994 A1 | 8/2014 |

OTHER PUBLICATIONS

Ebrahimi et al. Iranian Journal of Neurology 2012, 11 (4), 162-163.*
International Search Report with Written Opinion issued in International Application No. PCT/DK2016/050424 dated Feb. 28, 2017.
Extended European Search Report issued in EP Application No. 15199512.3 dated Mar. 11, 2016.
Martin J. Brodie, et al., Rufinamide for the adjunctive treatment of partial seizures in adults and adolescents: A randomized placebo-controlled trial, Epilepsia, 50(8):1899-1909, 2009.
Manuela Contin, et al., Simultaneous HPLC-UV analysis of rufinamide, zonisamide, lamotrigine, oxcarbazepine monohydroxy derivative and felbamate in deproteinized plasma of patients with epilepsy, Journal of Chromatography B, 878:461-465, 2010.
Kevin R. Novak, et al., Sodium channel slow inactivation as a therapeutic target for myotonia congenita, Annals of Neurology Journal, 77(2):320-332, Feb. 2015, doi:10.1002/ana.24331.
Martin SKOV, MSc et al., The Anti-Convulsants Lacosamide, Lamotrigine, and Rufinamide Reduce Myotonia in Isolated Human and Rat Skeletal Muscle, Muscle Nerve, 56:136-142, 2017.
Lamotrigine as Treatment of Myotonia—clinical trial—https://clinicaltrials.gov/ct2/show/NCT01939561.
Wang, "Manual of Clinical New and Specific Drugs," Jindun Publishing House, (Oct. 31, 2011), pp. 288.
Office Action (The First Office Action) dated Aug. 11, 2020, by the China National Intellectual Property Administration in corresponding Chinese Patent Application No. 201680080246.1 and an English Translation of the Office Action. (16 pages).
Gilchrist et al., "Nav 1.1 Modulation by a Novel Triazole Compound Attenuates Epileptic Seizures in Rodents," ACS Chemical Biology, (2014), vol. 9, No. 5, pp. 1204-1212.
Ito et al., "Treatment of Pediatric Epilepsy," Japanese Journal of Clinical Medicine, (May 2014), vol. 72, No. 5, pp. 845-852.
Logigian et al., "Mexiletine is an Effective Antimyotonia Treatment in Myotonic Dystrophy Type 1," Neurology, (2010) vol. 74, No. 18, pp. 1441-1448.
Nakatani et al., "The Effect of Lamotrigine on Nav1.4 Voltage-Gated Sodium Channels," Journal of Pharmacological Sciences, (2013), vol. 123, No. 2, pp. 203-206.
Novak et al., "Sodium Channel Slow Inactivation as a Therapeutic Target for Myotonia Congenita," Annals of Neurology, (Feb. 2015), vol. 77, No. 2, pp. 320-332.

(Continued)

*Primary Examiner* — Irina Neagu
(74) *Attorney, Agent, or Firm* — BUCHANAN INGERSOLL & ROONEY PC

(57) ABSTRACT

The present invention relates to Rufinamide (or active derivatives thereof) for use in the treatment of myotonia, such as myotonia congenita, paramyotonia congenita and myotonic dystrophy. The present invention also relates to a combinatorial composition comprising Rufinamide (or active derivatives thereof) and Lamotrigine (or active derivatives thereof) for use as a medicament.

15 Claims, 8 Drawing Sheets

(56) References Cited

OTHER PUBLICATIONS

Office Action (Notice of Reasons for Rejection) dated Nov. 10, 2020, by the Japanese Patent Office in corresponding Japanese Patent Application No. 2018-530025 and an English Translation of the Office Action. (22 pages).
Office Action (Notice of Reasons for Rejection) dated Mar. 16, 2021, by the Japanese Patent Office in corresponding Japanese Patent Application No. 2018-530025 and an English Translation of the Office Action. (14 pages).
Office Action (The Second Office Action) dated May 6, 2021, by the China National Intellectual Property Administration in corresponding Chinese Patent Application No. 201680080246.1 and an English Translation of the Office Action. (15 pages).

\* cited by examiner

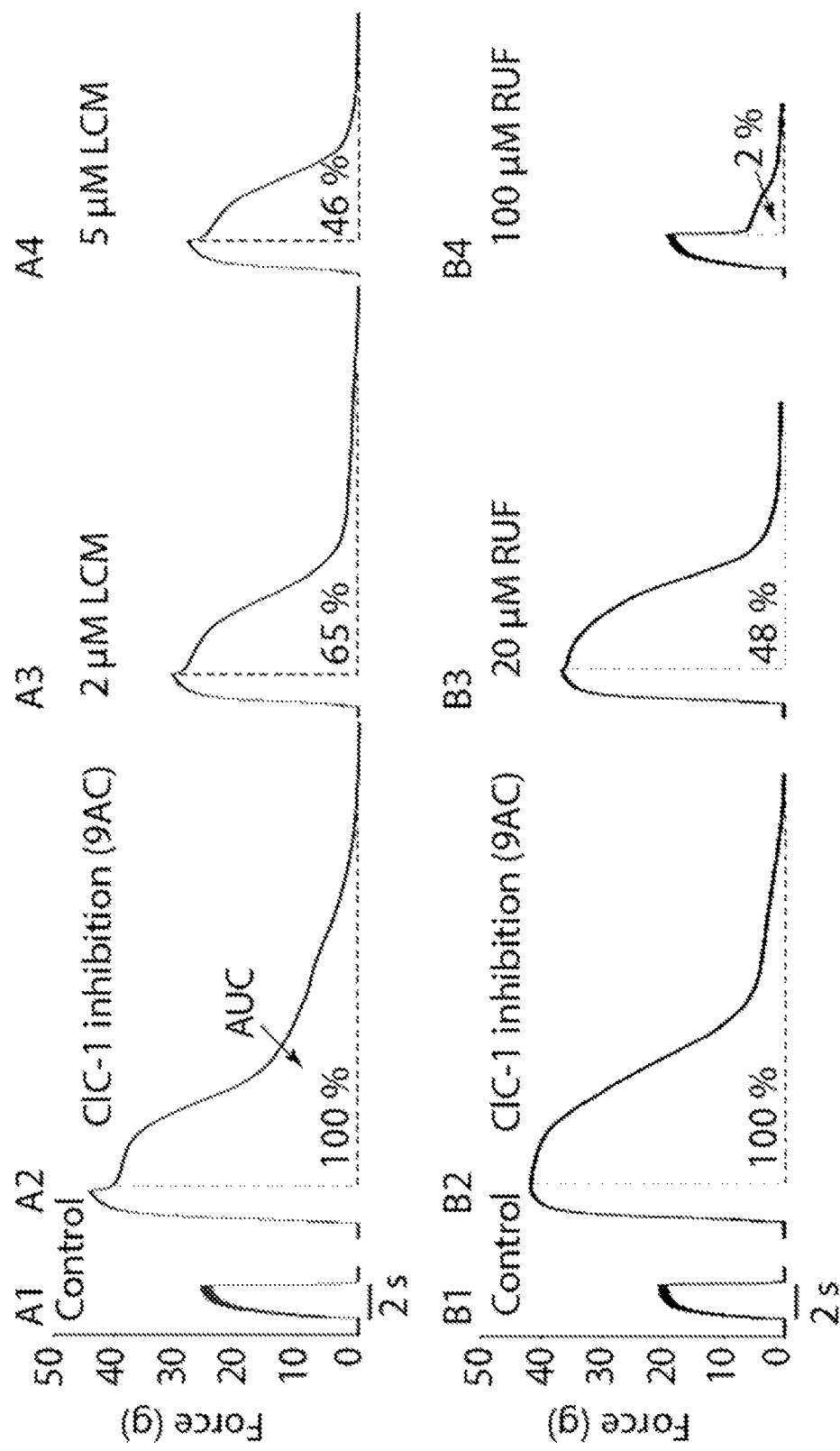
Fig. 1, continues

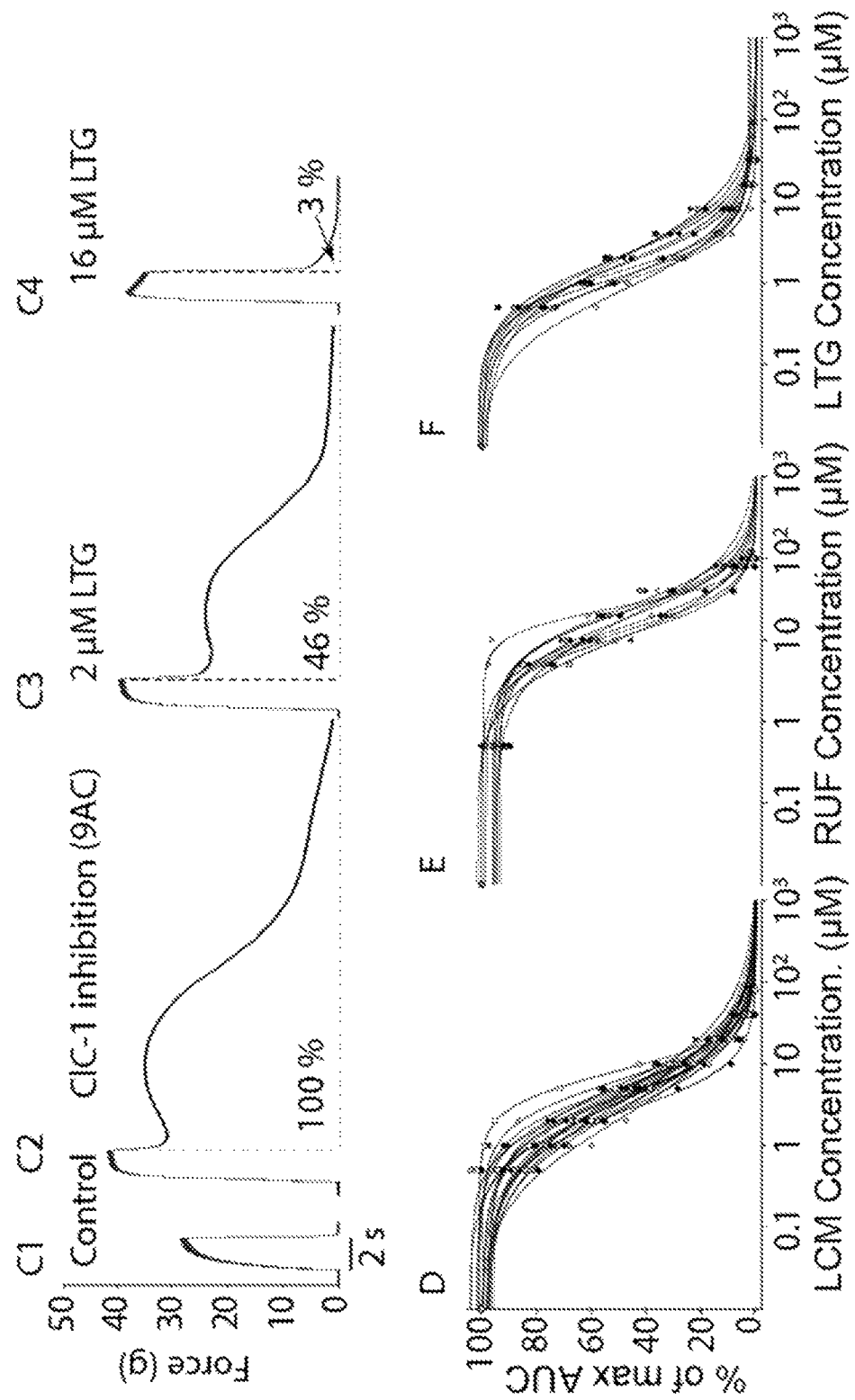
Fig. 1, continued

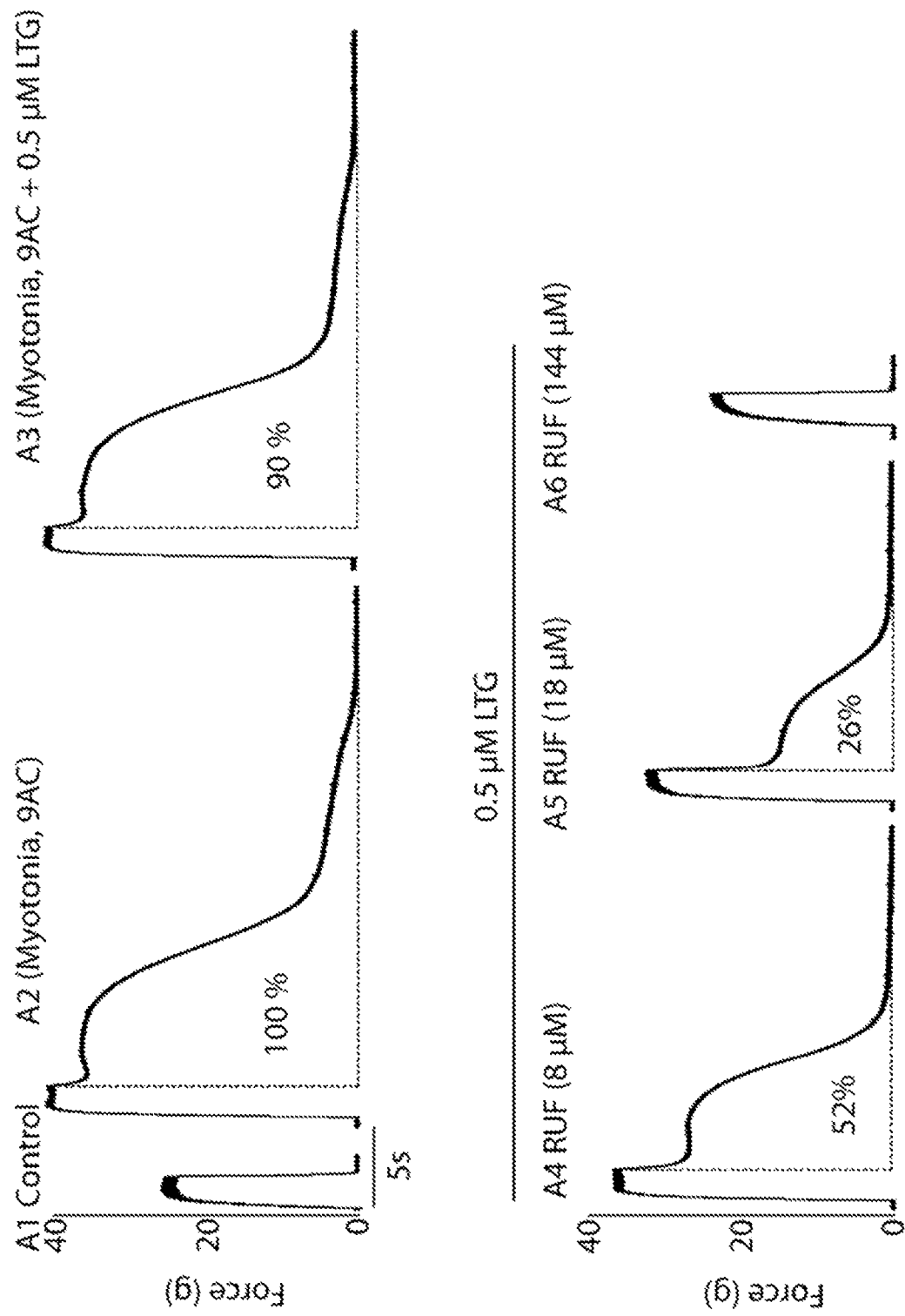
Fig. 3, continues

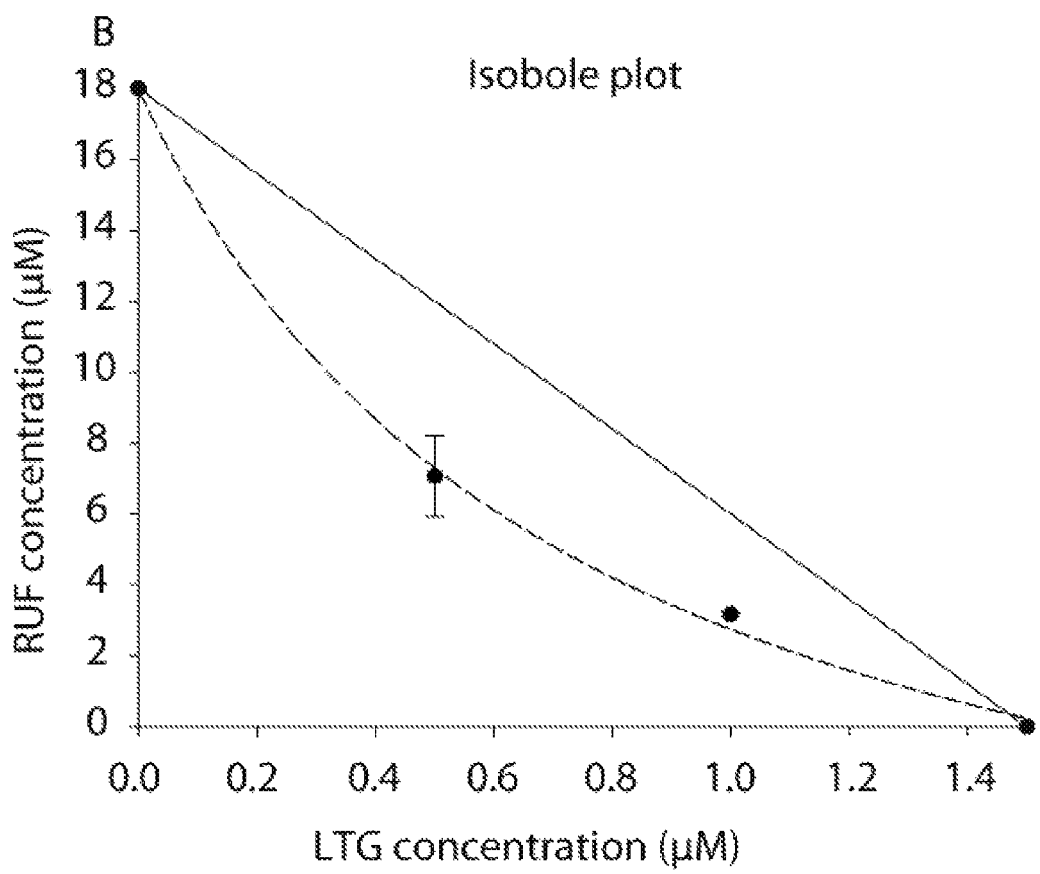
Fig. 3, continued

A
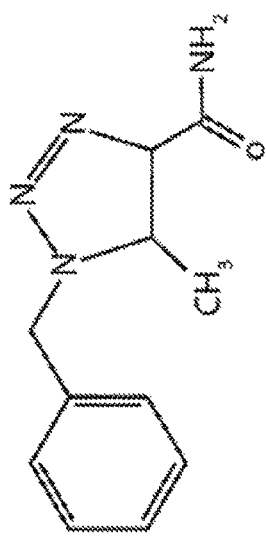
Compound 1
5-amino-1-benzyl-1H-1,2,3-triazole-4-carboxamide
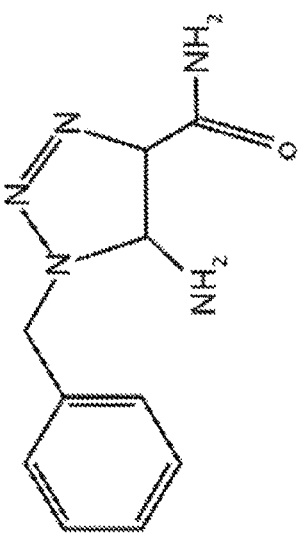
Compound 2
1-benzyl-5-methyl-1H-1,2,3-triazole-4-carboxamide
Fig. 5, continues

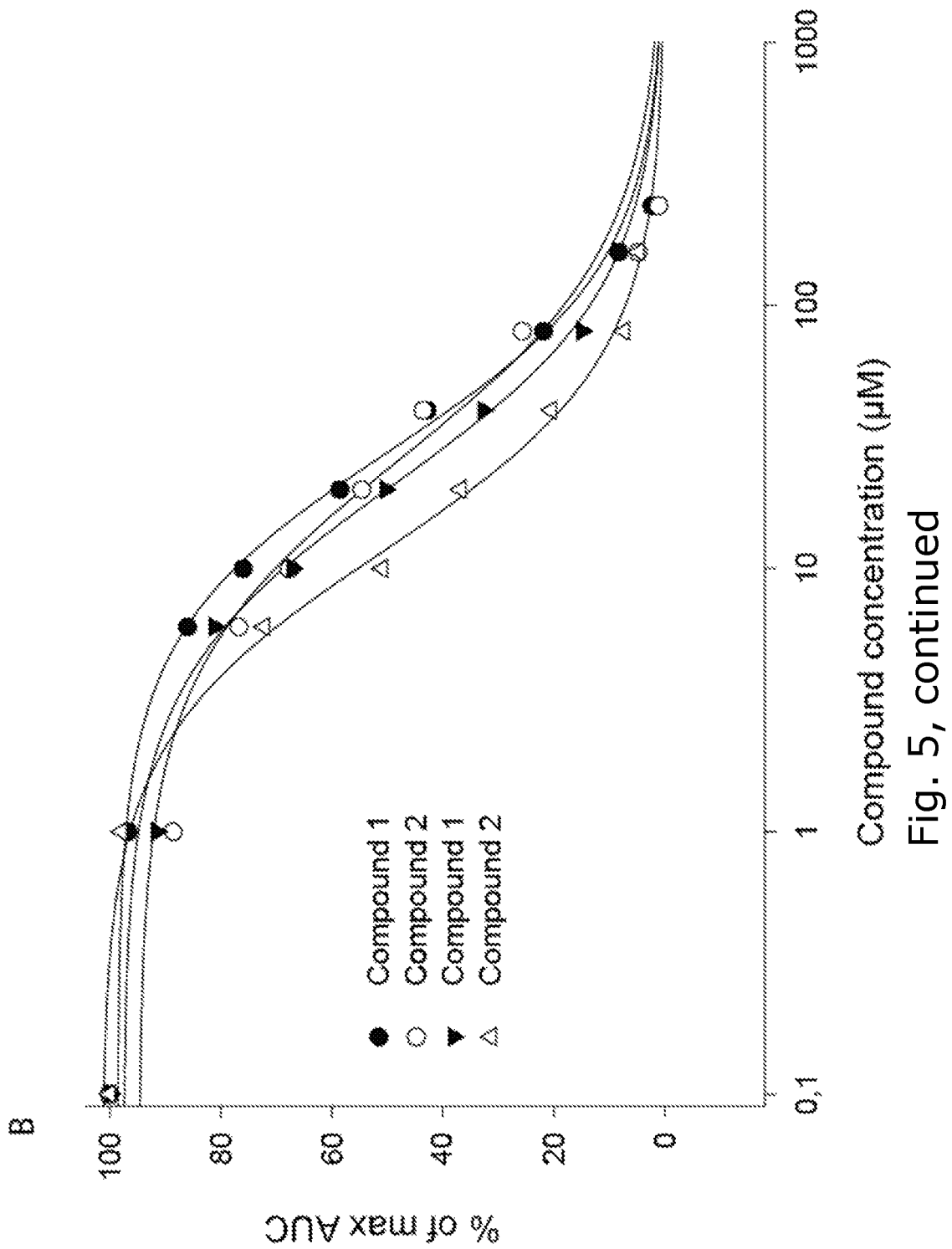
Fig. 5, continued

RUFINAMIDE FOR USE IN THE TREATMENT OF MYOTONIA

TECHNICAL FIELD OF THE INVENTION

The present invention relates to Rufinamide or derivatives thereof for use in the treatment of myotonia. In particular, the present invention relates to pharmaceutical compositions comprising Rufinamide or derivatives thereof for use in the treatment of Myotonia congenita, hyperkalaemic paralysis, hypokalaemic paralysis, Paramyotonia Congenita and myotonic dystrophy.

BACKGROUND OF THE INVENTION

Myotonia congenita and myotonic dystrophy are skeletal muscle disorders associated with loss of ClC-1 ion channel function. The ClC-1 channel dysfunction results in a large reduction in the membrane conductance of muscle fibres and, in turn, results in muscle fibre hyperexcitability. This hyperexcitability introduces spontaneous action potential excitations that triggers spontaneous contractions and delayed relaxation of muscle, which are the clinically hallmarks of myotonia. To alleviate myotonic symptoms, anti-myotonic treatment has generally focused on dampening the sodium current through the voltage gated sodium channels (NaV1.4) that are responsible for creating the upstroke of the action potential in muscle fibers. Pharmacologically, such Nav1.4 blockade has been accomplished with Mexilitine or Tocainide. However, both of these drugs have variable effects on myotonia, and they have been withdrawn from the market in some countries due to their adverse side effects. Therefore, there is currently no FDA-approved treatment for myotonia congenita. From this, it is clear that while Nav1.4 is a validated target in anti-myotonic treatment there is a need for new pharmaceutical approaches for inhibition or modulation of these channels.

EP0199262 (A2) discloses fluorinated benzyl triazole compounds and methods of producing such compounds.

Hence, an improved treatment of myotonia would be advantageous, and in particular a more efficient and/or reliable treatment of symptoms associated with myotonia would be advantageous.

SUMMARY OF THE INVENTION

The present study has used clinically approved anti-convulsant, sodium channel modulating drugs to test whether they can reduce myotonia in rat and human muscle. Specifically, it explores whether myotonia can be reduced by: i) a depolarising shift in the activation curve for Nav1.4, ii) a hyperpolarizing shift in the slow-inactivation curve, or facilitated entry into this state, and iii) a hyperpolarizing shift in the inactivation curve.

The present study shows that Lacosamide (LCM), Rufinamide (RUF) and Lamotrigine (LTG) were all capable of reducing myotonic contractions in ClC-1 inhibited rat and human muscles. Importantly, these anti-myotonic effects were observed at clinically accepted concentrations. The combination of LTG and RUF furthermore showed a clear synergistic anti-myotonic effect.

Thus, an object of the present invention relates to providing drugs/compositions for use in the treatment of myotonia.

Thus, one aspect of the invention relates to a (pharmaceutical) composition comprising Rufinamide or active derivatives thereof according to formula (I):

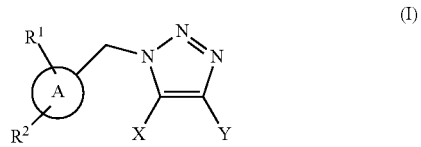

wherein,
A is an aryl or heteroaryl,
$R^1$ and $R^2$ are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, optionally $R^1$ and/or $R^2$ are absent,
X is selected from the group consisting of hydrogen, halogen, $C_1$-$C_5$ alkyl, $C_2$-$C_5$ alkenyl, $C_2$-$C_5$ alkynyl, optionally substituted ketone, optionally substituted aldehyde, and optionally substituted amine,
Y is selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide,
for use in the
treatment of myotonia; and/or
treatment or alleviation of symptoms associated with myotonia;
wherein said active derivatives thereof are capable of inhibiting and/or modulating the Nav1.4 voltage-gated sodium channel. In a preferred embodiment, the compound of formula (I) is Rufinamide.

A second aspect of the invention relates to a (pharmaceutical) composition comprising Rufinamide for use in the treatment of myotonia; and/or treatment or alleviation of symptoms associated with myotonia.

In an additional aspect, the invention relates to a (pharmaceutical) composition comprising Lacosamide (LCM) or Lamotrigine (LTG) for use in the treatment of myotonia; and/or treatment or alleviation of symptoms associated with myotonia. Preferably, the symptoms are muscle damage and/or muscle wasting.

Another aspect of the present invention relates to a (combinatorial) composition comprising
Rufinamide or active derivatives thereof according to formula (I):

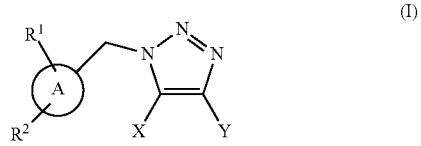

wherein,
A is an aryl or heteroaryl,
$R^1$ and $R^2$ are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amineoptionally $R^1$ and/or $R^2$ are not present,
X is selected from the group consisting of hydrogen, halogen, $C_1$-$C_5$ alkyl, $C_2$-$C_5$ alkenyl, $C_2$-$C_5$ alkynyl, optionally substituted ketone, optionally substituted aldehyde, and optionally substituted amine, Y is selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide, and Lamotrigine or active derivatives thereof according to formula (II)

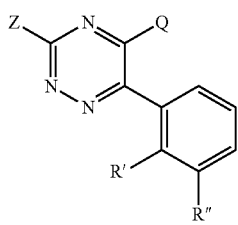

(II)

wherein,
- Z and Q are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide,
- R' and R" are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide, optionally R' and/or R" are absent, wherein said active derivatives thereof, are capable of inhibiting and/or modulating the Nav1.4 voltage-gated sodium channel. In a preferred embodiment, the compound of formula (I) is Rufinamide, and the compound of formula (II) is Lamotrigine.

Yet another aspect of the present invention is to provide a kit of parts comprising a first composition comprising Rufinamide or active derivatives thereof according to formula (I):

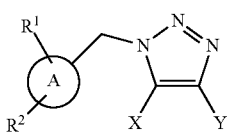

(I)

wherein,
- A is an aryl or heteroaryl,
- $R^1$ and $R^2$ are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, optionally $R^1$ and/or $R^2$ are absent,
- X is selected from the group consisting of hydrogen, halogen, $C_1$-$C_5$ alkyl, $C_2$-$C_5$ alkenyl, $C_2$-$C_5$ alkynyl, optionally substituted ketone, optionally substituted aldehyde, and optionally substituted amine,
- Y is selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide, and a second composition comprising Lamotrigine or active derivatives thereof; according to formula (II)

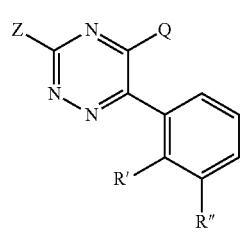

(II)

wherein,
- Z and Q are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide,
- R' and R" are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide, optionally $R^1$ and/or $R^2$ are absent, wherein said active derivatives thereof, are capable of inhibiting and/or modulating the Nav1.4 voltage-gated sodium channel, for use in the treatment of myotonia; and/or treatment or alleviation of symptoms associated with myotonia. In a preferred embodiment, the compound of formula (I) is Rufinamide, and the compound of formula (II) is Lamotrigine.

An additional aspect relates to a method of treating a subject in need of treatment of myotonia; and/or treatment or alleviation of symptoms associated with myotonia, the method comprising administrating a composition according to the invention to the subject.

BRIEF DESCRIPTION OF THE FIGURES

FIG. 1 shows that Lacosamide, Rufinamide and Lamotrigine reduce myotonia in rat soleus. A1, B1 and C1 all show the force responses to 15 Hz stimulation for 2 s with 0.2 ms pulses in representative isolated rat soleus muscles. A2, B2 and C2 show force responses to this stimulation after incubation with 9-AC to block ClC-1 channels and this introduces myotonia akin to myotonia congenita and myotonic dystrophy. The dotted line in A2 indicates cessation of stimulation and the force integral above this line was quantified as the myotonic response (Tail AUC). A3 and A4 show the myotonic response after adding 2 and 5 μM LCM, respectively. Similarly, B3 and B4 show response to 20 and 100 μM RUF, and C3 and C4 show force responses in the presence of 2 and 16 μM LTG. D shows AUC from individual muscles plotted as % of maximal AUC (A2, B2, C2) at a range of concentrations of LCM, with the 3-parameter sigmoidal fit for each muscle (n=20). E and F show similar data for RUF (n=10) and LTG (n=10), respectively.

FIG. 3 shows the synergistic effect of LTG and RUF. A1 shows the force response to 15 Hz stimulation for 2 s with 0.2 ms pulses, in isolated rat soleus muscles. A2 shows force response after incubation with 9-AC to block ClC-1 channels, introducing myotonia. A3 shows the force response in the presence of 9AC and 0.5 µM LTG. A4 shows the force response when i LTG was raised to 8 µM RUF. A5 and A6 show force response when RUF was further raised to 18 µM and 144 µM, respectively. B Shows an isobole plot that depicts the concentrations of RUF that was required to abolish 50% of maximal AUC in the presence of a given concentration of LTG. Two fixed concentrations of LTG were used to determine the synergy effect of RUF and LTG: 0.5 µM (n=6) and 1 µM (n=4). The dashed line shows the best hyperbolic fit to the data, indicating the expected RUF concentration to be used along with a given LTG concentration. The solid line indicates the concentration of RUF at any given LTG concentration that would be expected if the drugs acted purely in an additive manner. Data points below this line reflect that drugs act in a synergistic manner.

FIG. 5 shows schematic drawings of the two compounds, Compound 1 (5-amino-1-benzyl-1H-1,2,3-triazole-4-carboxamide) and Compound 2 (1-benzyl-5-methyl-1H-1,2,3-triazole-4-carboxamide), with UPAC name above each compound. B shows the relative area under the curve (AUC) from rat soleus muscle stimulated at 60 Hz, 2 s with 0.2 ms pulses, incubated with 9AC to induce myotonia by blocking ClC-1 channels. When myotonia had fully developed (100% AUC) the compounds were added at increasing concentrations, and myotonia was tested at each concentration (60 Hz, 2 s). Data from the experiments was fitted to a 3-parameter sigmoid function, and the resulting fit is shown as a solid line for each muscle. Each compound was tested on two muscles.

Figure 2:
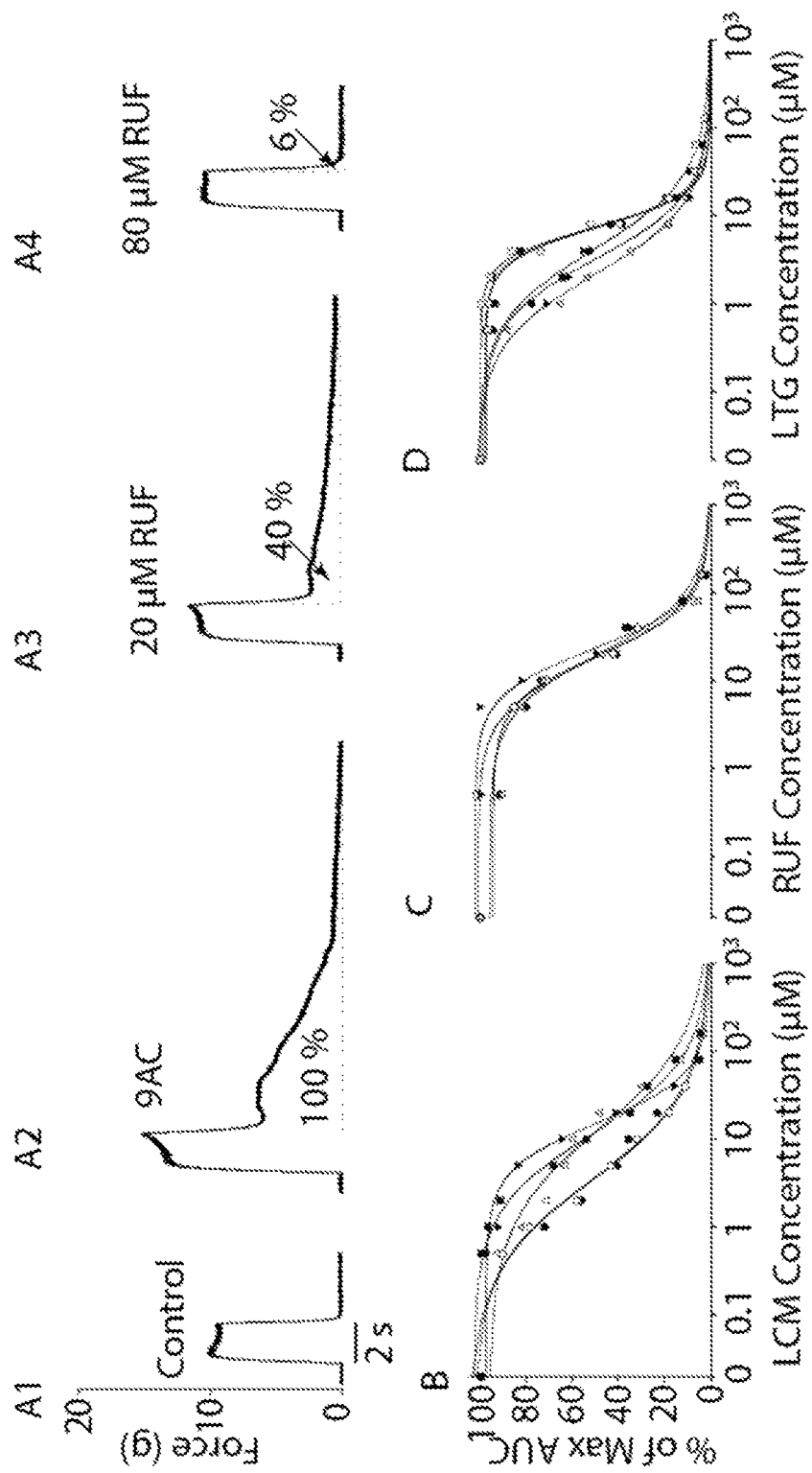
FIG. 2 shows that Lacosamide, Rufinamide and Lamotrigine reduce myotonia in isolated human abdominal rectus muscle. A1 shows force response from a bundle of human abdominal muscle stimulated for 2 s at 15 Hz by 0.2 ms pulses. As in rat muscles myotonia was induced with 9-AC and quantified from the AUC as determined from the cessation of stimulation to force returned to baseline. A2 shows the force response to block of ClC-1 channels with 9-AC. A3 shows the response to stimulation in the presence of 9AC and 20 µM RUF, and A4 shows the response in the presence of 9AC and 80 µM RUF. B Shows AUC from individual muscle bundles as % of maximal AUC (A2) at a range of concentrations of LCM, with 3 parameter sigmoidal fit for each muscle bundle (n=5). C and D show similar data for RUF (n=4) and LTG (n=6), respectively.

The present invention will now be described in more detail in the following.

DETAILED DESCRIPTION OF THE INVENTION

Definitions

Prior to discussing the present invention in further details, the following terms and conventions will first be defined:

Myotonia

Myotonia is a symptom of a small handful of certain neuromuscular disorders characterized by delayed relaxation (prolonged contraction) of the skeletal muscles after voluntary contraction or electrical stimulation.

Myotonia is present in Myotonia congenita, hyperkalaemic paralysis, hypokalaemic paralysis, Paramyotonia Congenita and myotonic dystrophy.

Myotonic Dystrophy

Myotonic dystrophy (dystrophia myotonica, myotonia atrophica) is a chronic, slowly progressing, highly variable, inherited multisystemic disease. It is an autosomal-dominant disease. It is characterized by wasting of the muscles (muscular dystrophy), cataracts, heart conduction defects, endocrine changes, and myotonia.

There are two main types of myotonic dystrophy. Myotonic dystrophy type 1 (DM1), also called Steinert disease, has a severe congenital form and an adult-onset form. Myotonic dystrophy type 2 (DM2), also called proximal myotonic myopathy (PROMM) is rarer than DM1 and generally manifests with milder signs and symptoms. Myotonic dystrophy can occur in people of any age. Both forms of the disease display an autosomal-dominant pattern of inheritance. Both DM1 and DM2 have adult-onset forms.

Myotonia Congenita

Congenital myotonia (also myotonia congenita), is a genetic, neuromuscular channelopathy that affects skeletal muscles (muscles used for movement). The hallmark of the disease is the failure of initiated contraction to terminate, often referred to as delayed relaxation of the muscles (myotonia) and rigidity. The disorder is caused by mutations in part of a gene (CLCN1) encoding the ClC-1 chloride channel, resulting in muscle fiber membranes to have an unusually exaggerated response to stimulation (hyperexcitability). Symptoms include delayed relaxation of the muscles after voluntary contraction (myotonia), and may include stiffness, hypertrophy (enlargement), transient weakness in some mutations, and cramping.

Paramyotonia Congenita

Paramyotonia Congenita results from mutation in the SCN4A gene encoding the voltage-gated sodium channel in skeletal muscle fiber membrane, Nav1.4. Mutations may alter the kinetics of the channel, such that the channel fails to inactivate properly, thus allowing spontaneous action potentials to occur after voluntary activity has terminated, prolonging relaxation of the muscle, or can result in paralysis if the relaxation is severely prolonged.

Rufinamide

Rufinamide (RUF) has the systematic UPAC name: 1-(2, 6-Difluorobenzyl)-1H-1,2,3-triazole-4-carboxamide. Trade names of Rufinamide are Banzel (US) and Inovelon (EU). Rufinamide may also be described by its chemical structure by formula (III):

Rufinamide is an anticonvulsant medication. It is used in combination with other medication and therapy to treat Lennox-Gastaut syndrome and various other seizure disorders.

Thus, in an embodiment Rufinamide is given by the formula (III):

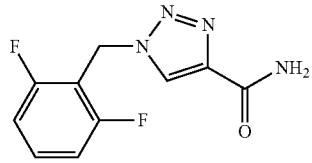

(III)

In another embodiment, Rufinamide is given by the formula (UPAC):
1-(2,6-Difluorobenzyl)-1H-1,2,3-triazole-4-carboxamide.

Lamotrigine

Lamotrigine (LTG) has the systematic UPAC name: 6-(2,3-dichlorophenyl)-1,2,4-triazine-3,5-diamine. Lamotrigine may also be described by its chemical structure by formula (IV):

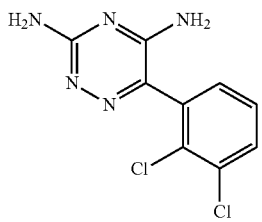

(IV)

Lamotrigine is marketed in most of the world as "Lamictal", Lamotrigine is an anticonvulsant drug used in the treatment of epilepsy and bipolar disorder. It is also used off-label as an adjunct in treating clinical depression. For epilepsy, it is used to treat focal seizures, primary and secondary tonic-clonic seizures, and seizures associated with Lennox-Gastaut syndrome.

Thus, in an embodiment, Lamotrigine is given by the formula (IV):

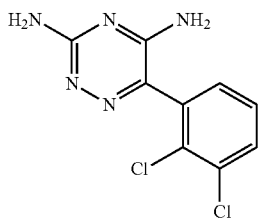

(IV)

In yet an embodiment, Lamotrigine is given by the formula (UPAC):
6-(2,3-dichlorophenyl)-1,2,4-triazine-3,5-diamine.

Lacosamide

Lacosamide (LCM) has the systematic UPAC name: $N^2$-acetyl-N-benzyl-D-homoserinamide. Lacosamide may also be described by its chemical structure by formula (V):

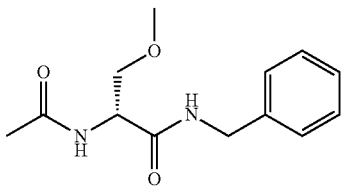

(V)

Lacosamide (LCM) (INN, formerly known as erlosamide, harkeroside, SPM 927, or ADD 234037) is a medication developed by Union Chimique Belge (UCB) for the adjunctive treatment of partial-onset seizures and diabetic neuropathic pain marketed under the trade name Vimpat.

Thus, in an embodiment, Lacosamide (LCM) is given by the formula (V):

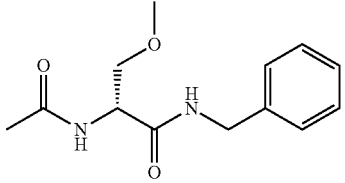

(V)

In yet an embodiment, Lacosamide (LCM) is given by the formula (UPAC):
$N^2$-acetyl-N-benzyl-D-homoserinamide.

Therapeutically Effective Amount

In the present context, the term "therapeutically effective amount" relates to a concentration or (daily) dosage, which is sufficient to treat myotonia, or treat or alleviate symptoms associated with myotonia.

Nav1.4 Voltage-Gated Sodium Channel

The Nav1.4 voltage-gated sodium channel is encoded by the SCN4A gene. Mutations in the gene are associated with hypokalemic periodic paralysis, hyperkalemic periodic paralysis, paramyotonia congenita, and potassium-aggravated myotonia.

Active Derivatives Thereof

In the present context, the term "active derivatives thereof" relates to compounds capable of inhibiting and/or modulating the Nav1.4 voltage-gated sodium channel.

Discussion

The present study aimed to evaluate the effect of three anticonvulsant drugs on myotonia in isolated muscle from rat and human. We found that Lacosamide (LCM), Lamotrigine (LTG) and Rufinamide (RUF) were all able to reduce myotonia within their clinically relevant concentration ranges. However, LCM was not able to reduce myotonia more than 60±2%, while RUF and LTG both reduced myotonia by 92±2%, within clinically observed concentration ranges. Clear synergistic effect on myotonia was observed for LTG and RUF.

The study also reveals that myotonia can cause pronounced muscle damage and that LTG and RUF can prevent this myotonia-induced damage. This was apparent from myotonia causing marked LDH release from myotonic muscles. LDH is a clinically used indicator of muscle damage and its elevation with myotonia in this study strongly suggests that myotonia contributes to the muscle damage and wasting in myotonic dystrophy. Since, RUF and LTG were both able to abolish myotonia and the myotonia-induced damage it is suggested that RUF and LTG could be used to reduce myotonia and thereby muscle wasting in myotonic dystrophy.

Composition Comprising Rufinamide for use in the Treatment of Myotonia

In a first aspect, the invention relates to a (pharmaceutical) composition comprising Rufinamide or active derivatives thereof according to formula (I):

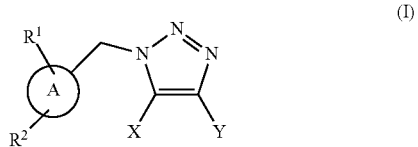

wherein,
A is an aryl or heteroaryl,
$R^1$ and $R^2$ are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, optionally $R^1$ and/or $R^2$ are absent,
X is selected from the group consisting of hydrogen, halogen, $C_1$-$C_5$ alkyl, $C_2$-$C_5$ alkenyl, $C_2$-$C_5$ alkynyl, optionally substituted ketone, optionally substituted aldehyde, and optionally substituted amine,
Y is selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide,
for use in the
treatment of myotonia; and/or
treatment or alleviation of symptoms associated with myotonia;
wherein said active derivatives thereof are capable of inhibiting and/or modulating the Nav1.4 voltage-gated sodium channel.

A second aspect of the invention relates to a (pharmaceutical) composition comprising Rufinamide for use in the treatment of myotonia; and/or treatment or alleviation of symptoms associated with myotonia.

As shown in examples 1, 2 and 4, Rufinamide (and Lamotrigine and Lacosamide) are capable of inhibiting myotonia in both rat and human muscles.

In an embodiment, A is selected from the group consisting of phenyl, pyridine, pyrimidine, pyridazine, pyrazine, pyrrole, pyrazole, imidazole, furane, and thiophene. In another embodiment, A is phenyl.

In yet another embodiment, $R^1$ and $R^2$ are in the 2- and 6- (ortho) positions of said phenyl. In a further embodiment, $R^1$ and $R^2$ are selected from the group consisting of halogen, methyl, and amine, preferably halogen. In yet a further embodiment $R^1$ and $R^2$ are fluorine. In a specific embodiment, $R^1$ and/or $R^2$ are absent (see example 5), thus $R^1$ and/or $R^2$ are H. In accordance with this specific embodiment, in yet a further embodiment the compound is 5-amino-1-benzyl-1H-1,2,3-triazole-4-carboxamide or 1-benzyl-5-methyl-1H-1,2,3-triazole-4-carboxamide.

In an embodiment, X is selected from the group consisting of hydrogen, halogen, methyl and amine, preferably hydrogen.

In another embodiment, Y is a carboxamide, preferably —C(O)NH$_2$.

In yet another embodiment, the optional further substituents are selected from the group consisting of halogen, methyl and amine.

In a preferred embodiment, the composition for use comprises Rufinamide and/or the compound of formula (I) is Rufinamide.

Different types of myotonia exist. Thus, in an embodiment, the myotonia is selected from the group consisting of myotonia congenita, paramyotonia congenita, myotonic hyperkalemic periodic paralysis (HPP) hyperkalaemic hypokalaemic paralysis, and myotonic dystrophy. In another embodiment, the myotonia is myotonia congenita or myotonic dystrophy. In yet an embodiment the myotonia is selected from the group consisting of myotonia congenita, myotonic dystrophy type 1 and myotonic dystrophy type 2.

Different types of symptoms are associated with myotonia. Thus, in an embodiment, said symptoms are selected from the group consisting of unwilling muscle contractions, muscle stiffening, arrest of movement, delayed relaxation of the muscles after voluntary contraction (myotonia), hypertrophy (enlargement), transient weakness, muscle damage, muscle atrophy, muscle wasting, and cramping, preferably muscle wasting. As further shown in example 4, Rufinamide and Lamotrigine are capable of inhibiting muscle damage in a rat model, tested by the release of LDH. Damage is a precursor for wasting.

The composition may further comprise other drugs. Thus, in yet an embodiment, the composition for use further comprises Lamotrigine or active derivatives thereof according to formula (II)

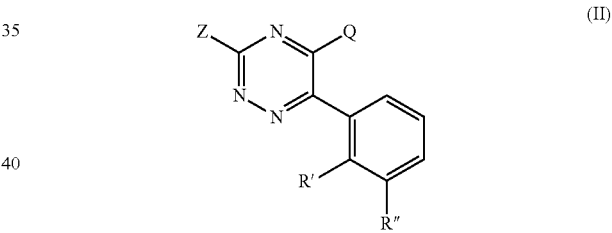

wherein,
Z and Q are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide,
R' and R" are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide, optionally R' and/or R" are absent,
wherein said active derivatives thereof, are capable of inhibiting and/or modulating the Nav1.4 voltage-gated sodium channel.

In an embodiment, Z and Q are both amine.

In another embodiment, R' and R" are amine, methyl, or halogen. In yet another embodiment R' and R" are both halogen. In a further embodiment R' and R" are both chlorine. In a specific embodiment, R' and/or R" are absent (see example 5).

In yet another embodiment, Z and Q are both amine, and R' and R" are both chlorine.

In yet another embodiment, the optional further substituents are selected from the group consisting of halogen, methyl and amine.

In a preferred embodiment, the compound of formula (I) is Rufinamide, and the compound of formula (II) is Lamotrigine.

In yet a preferred embodiment, the combined inhibition and/or modulation of the Nav1.4 voltage-gated sodium channel achieved when administering the combinatorial composition according to the invention is greater than the sum of the inhibition and/or modulation achieved when administering the compound of formula (I) and the compound of formula (II) separately. In short, a synergistic effect is obtained. As shown in example 3, a clear synergistic effect between Rufinamide and Lamotrigine is documented by the use of an isobole plot.

In yet an embodiment, the composition further comprises Lacosamide (LCM) or active derivatives thereof, wherein said active derivatives thereof, are capable of inhibiting and/or modulating the Nav1.4 voltage-gated sodium channel.

The symptoms associated to myotonia may arise from different cellular defects. Thus, in a further embodiment the symptoms associated with myotonia is associated to mutations in the gene (CLCN1) encoding the ClC-1 chloride channel and/or lowered protein expression and/or failure to express the ClC-1 due to ClC-1 mRNA aggregation.

The composition may be administered to a subject by different routes. Thus, in an embodiment the composition is administered orally, topically, subcutaneously or intravenously. Preferably, the composition is orally administered such as in the form of a tablet. It is to be understood that the subject preferably is a mammal, and most preferably is a human.

The daily dosage of Rufinamide may vary. Thus, yet a further embodiment, the composition for use comprises Rufinamide or active derivatives thereof at a therapeutically effective amount, such as in a daily dosage in the range 10-7200 mg/day, such as 400-3600 mg/day, such as 100-2100 mg/day or such as 1600-7200 mg/day.

The composition may be further optimized. Thus, in an embodiment the composition for use further comprises a pharmaceutically acceptable adjuvant, diluent, and/or carrier.

Composition comprising Rufinamide and Lamotrigine

As shown in example 3, a surprising synergistic effect between Rufinamide and Lamotrigine in the treatment of myotonia is disclosed. Thus, further aspect of the invention relates to a (combinatorial) composition comprising Rufinamide or active derivatives thereof according to formula (I):

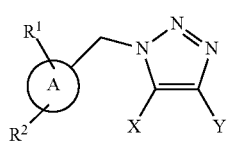
(I)

wherein,

A is an aryl or heteroaryl, $R^1$ and $R^2$ are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, optionally $R^1$ and/or $R^2$ are absent, X is selected from the group consisting of hydrogen, halogen, $C_1$-$C_5$ alkyl, $C_2$-$C_5$ alkenyl, $C_2$-$C_5$ alkynyl, optionally substituted ketone, optionally substituted aldehyde, and optionally substituted amine, Y is selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide, and Lamotrigine or active derivatives thereof according to formula (II)

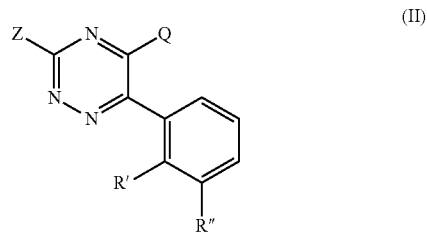
(II)

wherein,

Z and Q are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide, R' and R" are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide, optionally R' and/or R" are absent, wherein said active derivatives thereof, are capable of inhibiting and/or modulating the Nav1.4 voltage-gated sodium channel.

It is of course to be understood that A, X, Y, Z, N, Q, R' and R" may be selected as previously defined for the previous aspects of the invention.

A further aspect relates to this combinatorial composition for use as a medicament. In yet a further aspect relates to this combinatorial composition for use in the treatment of myotonia; and/or treatment or alleviation of symptoms associated with myotonia.

Yet a further aspect relates to this combinatorial composition further comprising a pharmaceutically acceptable adjuvant, diluent, and/or carrier.

An embodiment also relates to the combinatorial composition according to the invention comprising Rufinamide or active derivatives thereof according to formula (I), at a therapeutically effective amount; and Lamotrigine or active derivatives thereof according to formula (II), at a therapeutically effective amount.

In yet another embodiment the therapeutically effective amount is sufficient to treat myotonia, or treat or alleviate symptoms associated with myotonia. The symptoms are as previously described.

A more specific embodiment of the invention, relates to the combinatorial composition according to the invention comprising 5-7200 mg Rufinamide or active derivatives thereof according to formula (I); and 5-800 mg Lamotrigine or active derivatives thereof according to formula (II).

Kit of Parts

The combinatorial treatment may be administered simultaneously or in any order to achieve the desired treatment as outlined above.

Thus yet an aspect of the invention relates to a kit of parts comprising a first composition comprising Rufinamide or active derivatives thereof according to formula (I):

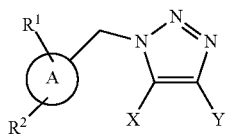

wherein,

A is an aryl or heteroaryl, $R^1$ and $R^2$ are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, optionally $R^1$ and/or $R^2$ are absent, X is selected from the group consisting of hydrogen, halogen, $C_1$-$C_5$ alkyl, $C_2$-$C_5$ alkenyl, $C_2$-$C_5$ alkynyl, optionally substituted ketone, optionally substituted aldehyde, and optionally substituted amine, Y is selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide, and a second composition comprising Lamotrigine or active derivatives thereof; according to formula (II)

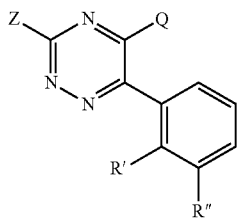

wherein,

Z and Q are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide, R' and R" are independently selected from the group consisting of halogen, $C_1$-$C_5$ alkyl, $C_2$-$C_5$ alkenyl, $C_2$-$C_5$ alkynyl, optionally substituted ketone, optionally substituted aldehyde, and optionally substituted amine, carboxylic acid and carboxamide, optionally R' and/or R" are absent, wherein said active derivatives thereof, are capable of inhibiting and/or modulating the Nav1.4 voltage-gated sodium channel, for use in the treatment of myotonia; and/or treatment or alleviation of symptoms associated with myotonia.

It is of course to be understood that A, X, Y, Z, N, Q, R' and R" may be selected as previously defined for the previous aspects of the invention.

In a preferred embodiment, the compound of formula (I) is Rufinamide, and the compound of formula (II) is Lamotrigine.

It should be noted that embodiments and features described in the context of one of the aspects of the present invention also apply to the other aspects of the invention. This in particular, relates to the described formulas, and possible substituents.

All patent and non-patent references cited in the present application, are hereby incorporated by reference in their entirety.

The invention will now be described in further details in the following non-limiting examples.

EXAMPLES

Example 1

Aim

To test whether Rufinamide (RUF), Lamotrigine (LTG) and Lacosamide (LCM) can abolish myotonia induced by ClC-1 inhibition in rat soleus muscles.

Methods

Animal Handling

No experiments were performed on live animals, and all handling and killing of animals complied with Danish animal welfare regulations and the local guidelines for animal handling at Aarhus University. Contractile force was measured in soleus muscles after dissection from young 4-week-old male/female Wistar rats (65-75 g) that were obtained from Janvier laboratories. All animals were fed ad libitum and kept at constant temperature (21° C.) and day length (12 h).

Solutions and Compounds

The standard Krebs-Ringer solution used for incubation during experiments contained (mM): 122 NaCl, 25 $NaHCO_3$, 2.8 KCl, 1.2 $KH_2PO_4$, 0.6 $MgSO_4$, 1.27 CaCl2 and 5 D-glucose. In all experiments, solutions were maintained at 30° C. and equilibrated with a mixture of 95% $O_2$ and 5% $CO_2$ (pH~7.4). To induce experimental myotonia, 100 µM of the ClC-1 channel inhibitor 9-anthracene-carboxylic acid (9AC) (Sigma Aldrich, DK) dissolved in DMSO (Sigma Aldrich, DK) was added to the incubation solution. The final DMSO concentration never exceeded 0.35%.

Measurement of Contractile Force

The force produced during isometric contractions of the muscles was recorded using an experimental setup that has previously been described in detail (Skov M, Riisager A, Fraser J A, Nielsen O B, Pedersen T H. Extracellular magnesium and calcium reduce myotonia in ClC-1 inhibited rat muscle. Neuromuscular Disorders 2013 06; 23(6):489-502). Briefly, field stimulation across the central part of the muscle (0.2 ms pulses, 24-30 V/cm) was used to trigger contractile activity. At the beginning of incubation in the experimental chambers, the muscles were stretched to the length that resulted in maximum active twitch force (2 Hz). In all experiments, muscles were stimulated every 10 min at 15 Hz for 2 s. To quantify myotonic behaviour of the muscles, including increased force and prolonged relaxation, the force-time integral of the active force responses (area under curve, AUC) was determined for each contraction, with the active force being calculated as the difference between the total and the resting force after cessation of electrical stimulation. To assess the effect of LCM, RUF and LTG on myotonia the tail AUC of the force response was used. This corresponds to the AUC from cessation of stimulation-induced contraction until full relaxation (see FIG. 1 in example 1). To determine the dose-response relationship of between myotonia and drug, muscles were incubated with 9AC and stimulated until a stable myotonic phenotype had developed (usually 5-7 stimulations). Muscles were then incubated at progressively increasing concentration of drug with each drug concentration being tested for at least 30 min (three stimulations), before further increase in concentration. In experiments where combinations of drugs were tested, muscles were incubated for 30 min at every combination of drugs before evaluating the effect of the drugs. After this the drug concentrations were further increased.

Statistical Analysis

All average data is presented as means with SEM. Statistically significant difference between two data groups was ascertained using Student's two-tailed t test for paired or un-paired observations as appropriate. One way analysis of variance (ANOVA) was used for comparison of more than two data groups with Holm-Sidak post hoc test to detect significant differences between individual groups. P-values of less than 0.05 were considered to indicate significant difference between tested groups. Data from dose-response experiments were fitted to a 3 parameter sigmoidal function to get the concentration were half the myotonia had been suppressed ($EC_{50}$, Table 1).

Results

Isolated Rat Soleus

To first test for effects of the three drugs (RUF, LCM and LTG) on force in non-myotonic rat soleus muscles, muscles were exposed to 2 s stimulations at both 5 Hz and 60 Hz every 10 mins during three hrs of drug incubation. The drug concentrations were the highest free concentrations that are tolerated clinically: For both 5 and 60 Hz stimulation, incubation with 5 µM LCM reduced force by ~6-8% in two muscles. With 25 µM LTG force was reduced by ~6% in three muscles, and with 100 µM RUF force was reduced by 4% in three muscles. In all cases, these reductions in force during the three hours were similar to reductions observed in time-matched control muscles.

In the first series of experiments assessing for effects of RUF, LCM and LTG on myotonia, the myotonic phenotype was induced by incubating the muscles with either 100 µM of the ClC-1 channel blocker 9AC, or by reducing Cl⁻ concentration in the bathing solution to 30 (n=8) or 10 (n=8) mM (rat soleus, LCM treated). These approaches for reducing ClC-1 function were taken to resemble the ClC-1 dysfunction in myotonia congenita and myotonic dystrophy. Accordingly, incubation with 9AC or reduction in Cl⁻ concentration resulted in marked prolongation of relaxation, and increased maximal force when stimulated at 15 Hz for 2 s, as exemplified by FIG. 1 (A1, B1 and C1 vs. A2, B2 and C2). The addition of 2 µM LCM to the incubation solution reduced AUC by ~40%, FIG. 1 (A2 vs. A3). Increasing the LCM concentration to 5 µM reduced AUC by another ~20% (FIG. 1 A4). Likewise addition of 20 µM RUF to 9AC treated muscles reduced AUC by more than 50% (FIG. 1 B2 vs. B3), and when RUF concentration was increased to 100 µM the AUC was reduced by ~98% (FIG. 1 B4). Finally, addition of 2 µM LTG reduced AUC by ~46% at (FIG. 1 C3) and when LTG concentration was increased to 16 µM the AUC was reduced by ~98% (FIG. 1 C4). All three anti-convulsants (drugs) were able to completely abolishing myotonia if their concentrations were increased sufficiently. To quantify the dose dependency of the drugs on myotonia, the AUCs at different drug concentrations were plotted against drug concentration and the resulting plots of drug concentration versus degree of myotonia are shown for each drug in FIGS. 1D, E and F for LCM, RUF and LTG, respectively. Curves resulting from fitting data to a 3-parameter sigmoid equation are shown for individual muscles in each treatment group in FIG. 1D-F. Drugs were tested at concentrations that cover the whole clinical range (in µM); LCM from 0.5 to 80, LTG from 0.5 to 32 and RUF from 0.5 to 120. In every single muscle tested did AUC decline with increasing concentrations of drug. The concentration required to reduce AUC to 50% of maximal value ($EC_{50}$) are listed in Table 1 for each drug.

TABLE 1

| Rat | Drug | $EC_{50}$ | Slope of fit |
| --- | --- | --- | --- |
| n = 20 | Lacosamide | 5.02 ± 0.41 | −0.46 ± 0.031 |
| n = 10 | Lamotrigine | 1.52 ± 0.13 | −0.39 ± 0.042 |
| n = 10 | Rufinamide | 18.06 ± 1.84 | −0.29 ± 0.02 |

Conclusion

Overall, these results show that the three anti-convulsants (Lacosamide, Lamotrigine and Rufinamide) are able to completely abolish myotonia in a dose depending manner in a rat model.

Example 2

Aim

To investigate if the three anti-convulsant drugs (Rufinamide (RUF), Lamotrigine (LTG) and Lacosamide (LCM)) are capable of reducing myotonia in human muscles.

Methods

Human Tissue

The use of human muscles was approved by the Danish Ethics Committee, Region Midtjylland, Comité I (reference number 1-10-72-20-13) and was performed in accordance with the Helsinki Declaration. Informed consent was obtained from all subjects before inclusion. Muscles were obtained from 4 male subjects admitted in relation to planned aortic aneurysm surgery at Skejby hospital. Isolation of tissue from subjects was performed as described earlier (Skov M, De Paoli F V, Lausten J, Nielsen O B, Pedersen T H. Extracellular magnesium and calcium reduce myotonia in isolated ClC-1 chloride channel-inhibited human muscle. Muscle Nerve. 2015 January; 51(1):65-71). After isolation the tissue was transported to the laboratory at the University (<30 min) in a HEPES based solution (pH 7.4) at ~5° C. Upon arrival to the laboratory, the tissue was incubated in often-replaced fresh Krebs-Ringer bicarbonate solution equilibrated with 5% $CO_2$ in oxygen at 30° C. for 10 to 20 min, before further dissection into smaller bundles of approx. 4 cm length weighing 515±61 mg. For contraction experiments, bundles were tied at both ends with polyester string, to enable mounting of the preparations in the setups for measurement of contractile force.

Solutions, Contraction Setup, Data Analysis and Statistics

As in Example 1.

Results

The experiments in FIG. 1 were repeated for small muscle bundles of human abdominal muscle. 9AC was used to induce myotonia and, subsequently, LCM, RUF or LTG were added at increasing concentrations. In all cases, myotonia was reduced with increased concentration of drug. FIG. 2A shows traces from a single bundle of isolated human muscle stimulated at 15 Hz for 2 s before and after exposure to RUF. Myotonia was induced by incubation with 100 μM 9AC, and subsequent additions of RUF reduced myotonia gradually with almost full abolishment of myotonia at 80 μM. Similar traces were obtained with LCM- and LTG-treated bundles of human muscle. FIG. 2B-D show data and sigmoidal fits from individual bundles with additions of LCM (n=5), RUF (n=5) and LTG (n=6), respectively. The concentrations required to reduce AUC to 50% of maximal value ($EC_{50}$) are listed in Table 2 for each drug.

TABLE 2

| Human | Drug | $EC_{50}$ | Clinical max dose (μM) | Slope of fit |
|---|---|---|---|---|
| n = 5 | Lacosamide | 9.24 ± 2.54 | 5.7 | −0.44 ± 0.047 |
| n = 6 | Lamotrigine | 5.54 ± 0.88 | 25 | −0.30 ± 0.068 |
| n = 4 | Rufinamide | 22.47 ± 1.73 | 100 | −0.33 ± 0.035 |

Conclusion

Overall, these results show that the three anticonvulsants (Lacosamide, Lamotrigine and Rufinamide) are able to completely abolish myotonia in a dose dependent manner in isolated human muscles.

Example 3

Aim

To determine if the drugs had additive or synergistic effects on myotonia.

Methods

As described in Example 1.

Results

Effect of Combining Drugs

Rufinamide, Lamotrigine and Lacosamide all reduced myotonia at concentrations that are within the observed free serum concentrations in patients. However, while Lacosamide had to be raised above clinically accepted concentrations to abolish myotonia, the concentrations of Lamotrigine and Rufinamide that were required to abolish myotonia were well within the clinically accepted ranges.

To determine if additive or synergistic effects could be observed when drugs were combined, experiments with the following combinations of drugs were next performed: LCM-RUF, LCM-LTG, LTG-RUF and all three together. In all these experiments, rat soleus muscles were used.

As with either drug alone, a marked reduction in AUC was observed with any combination of drugs. Hence, combining 2 μM LCM with 9 μM RUF, which roughly corresponded to half the $EC_{50}$ values for these drugs (Table 1), the AUC of the isolated myotonic muscle was reduced by 58±9%. When concentrations were raised to 4 μM LCM and 18 μM RUF, the AUC was reduced by 88±1.3% and when concentration were finally raised to 150% of their $EC_{50}$ values, the AUC was reduced by 95±0.45%. Likewise, incubation with 4 μM LCM and 1.5 μM LTG resulted in a reduction in AUC by 79±3.6% and with 1.5 μM LTG and 18 μM RUF the AUC was reduced by 74±6.9%. When muscles were incubated with all three drugs at $EC_{50}$ values of each drug, the AUC was reduced by 87±2.1%.

Figure 4:
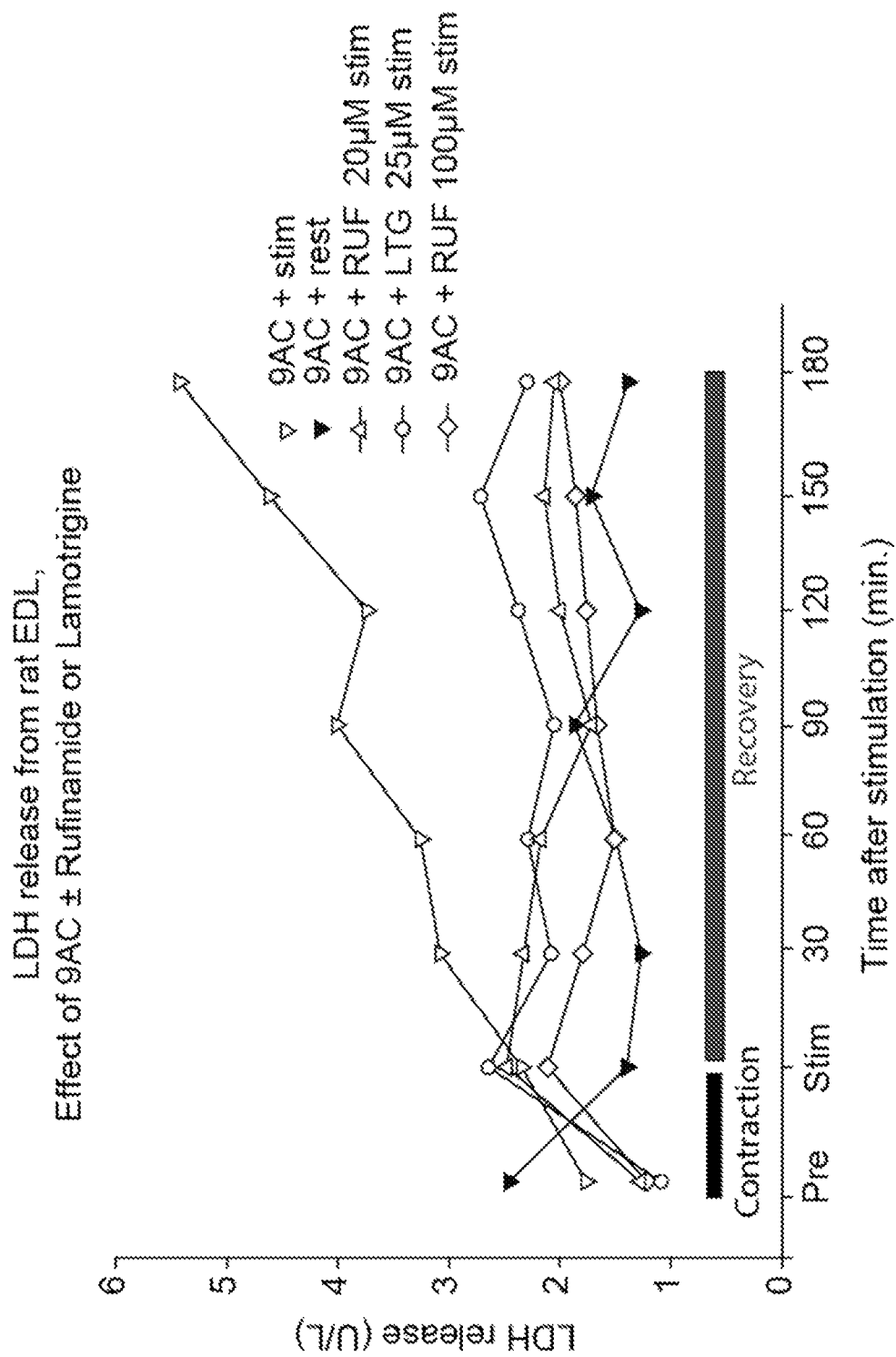
FIG. 4 shows effects of myotonia and RUF or LTG on release of lactate dehydrogenase (LDH), an indirect measure of damage from rat EDL muscles. In all cases a sample was taken before stimulation (Pre), the muscles were then stimulated to contraction for 2 s at 30 Hz by 0.2 ms pulses every 3 minutes for 60 min (20 stimulations) or left resting. Open symbols are from muscles incubated with 9AC±LTG or RUF. Solid triangles are from muscles incubated with 9AC without stimulation. Immediately after cessation of stimulation, a new sample was taken from solution incubating the muscles. For the next 180 minutes a sample was taken from the incubating solution every 30 minutes, as designated by the time after stimulation. The period from cessation of stimulation to 180 min after stimulation is termed recovery.

To test for synergistic effects of RUF and LTG a series of experiments were conducted that enabled a drug isobole to be determined. In these experiments rat soleus muscles were first exposed to 9AC to induce the myotonic phenotype (FIG. 3 A1 vs A2). Then 0.5 μM LTG was added and this resulted in a slight reduction in AUC to 90% of the full myotonic state (FIG. 3 A2 vs A3). Muscles were next subjected to increasing concentrations of RUF to determine the $EC_{50}$ value under these conditions of a low concentration of LTG (0.5 μM LTG). FIG. 3A4 shows that at 0.5 μM LTG, the RUF concentration only had to be raised to 7 μM RUF for AUC to be reduced by 50%. Such experiments were also conducted with pre-incubation with 1 μM LTG and under these conditions 3.1 μM RUF was enough to reduce AUC by 50%. To determine if the combined actions of LTG and RUF could be considered synergistic, these observations were used to construct an isobole plot (Tallarida R J. Revisiting the isobole and related quantitative methods for assessing drug synergism. J. Pharmacol. Exp. Ther (US, 2012) July; 342(1) 2-8.) In such plots the abscissa and ordinate show drug concentrations of the two explored drugs. The $EC_{50}$ for the drugs when administered alone are connected with a simple line. This line is then considered to reflect the concentrations of drugs that will have half effect if the drugs are simply additive in action. The area below the line reflects drug combinations for synergistic drug effects while the area above the line reflect antagonistic drug interaction. As can be seen from FIG. 3B, the 7 μM RUF at 0.5 μM LTG was in fact 5 μM less than what was expected if RUF and LTG acted purely additively, and 3.1 μM RUF at 1 μM LTG was 3 μM less than predicted by the assumption of additivity.

Thus in both cases the RUF concentration needed to be added to reach half effect was around 50% of the concentration that would be expected if the drugs had additive modes of action. This clearly demonstrates that LTG and RUF act synergistically on dampening myotonia.

Conclusion

The presented data shows that Lamotrigine and Rufinamide act synergistically on dampening myotonia.

Example 4

Aim

To determine the effect of Rufinamide and Lamotrigine on muscle damage that can induce wasting in vivo.

Methods

LDH Release Measurement

EDL muscles from rats were isolated and placed in small chambers with oxygenated as previously described in detail (Gissel H1, Clausen T. Excitation-induced Ca(2+) influx in rat soleus and EDL muscle: mechanisms and effects on cellular integrity. Am J Physiol Regul Integr Comp Physiol. 2000 279(3):R917-24).

Results

To explore for an effect of myotonia on muscle fibre integrity and the effect of the drugs hereupon, the release of the intracellular protein from the muscle, lactate dehydrogenase (LDH), to the incubation solution was determined in contracting EDL muscles. Muscles were stimulated at 15 Hz for 2 s by 0.2 ms pulses every 5 min for 60 min (12 stimulations) and the released LDH was determined before contractions and during 3 hrs after the contraction.

As clearly illustrated in FIG. 4, LDH release was only increased after stimulation from muscles if they had been rendered myotonic with 9AC and this myotonia-induced LDH release could be completely blocked with RUF. Very similar effects were observed with LTG.

Conclusion

The presented data show that Rufinamide and Lamotrigine are capable of inhibiting LDH release, thereby clearly indicating that these drugs may prevent muscle damage, the precursor for muscle wasting in vivo.

Example 5

Aim

To determine if analogues of Rufinamide had anti-myotonic effects:

UPAC formula names of compounds:

(1): 5-amino-1-benzyl-1H-1,2,3-triazole-4-carboxamide (2): 1-benzyl-5-methyl-1H-1,2,3-triazole-4-carboxamide Compounds are shown in FIG. 5

Methods

As described in Example 1.

Results

In isolated rat soleus muscle, the myotonic phenotype was induced by incubating the muscles with 100 μM of the ClC-1 channel blocker 9AC, and stimulating them at 15 Hz for 2 s by 0.2 ms pulses every 10 min. After myotonia had developed muscles were incubated at increasing concentrations of the two compounds 1 and 2. The resulting reduction in AUC is shown in FIG. 5B. Both compounds were able to completely abolish myotonia. The $EC_{50}$ values for the compounds were 24.7 μM for 1 and 19.1 μM for 2.

Conclusion

The presented data shows that the two analogues of Rufinamide are able to reduce myotonia in a dose dependent manner similar to that of Rufinamide.

ABBREVIATIONS

9AC, 9-anthracenecarboxylic acid;

AUC, area under the curve;

LCM, Lacosamide, [(2R)-2-acetamido-N-benzyl-3-methoxy-propanamide];

LTG, Lamotrigine, [6-(2,3-Dichlorophenyl)-1,2,4-triazine-3,5-diamine];

RUF, Rufinamide, [1-(2,6-Difluorobenzyl)-1H-1,2,3-triazole-4-carboxamide];

The invention claimed is:

1. A composition comprising
a compound according to formula (I):

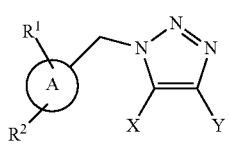

(I)

wherein,
A is an aryl that is a substituted phenyl ring,
$R^1$ and $R^2$ are each a halogen that is a fluorine,
X is a hydrogen, and
Y is a carboxamide that is —$CONH_2$,
and
a compound according to formula (II)

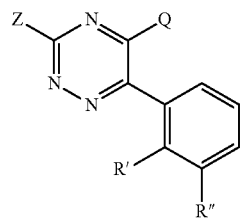

(II)

wherein,
Z and Q are each a $NH_2$, and
R' and R" are each a halogen that is a chlorine; and
wherein a molar ratio of the compound according to formula (I) and the compound according to formula (II) is in a range from 7:0.5 to 3.1:1.

2. A method for the treatment of myotonia and/or the treatment or alleviation of symptoms associated with myotonia comprising administering to a subject in need thereof a composition according to claim 1.

3. The method according to claim 2, wherein the compound of formula (I) is Rufinamide, and the compound of formula (II) is Lamotrigine.

4. The composition according to claim 1, wherein the compound of formula (I) is Rufinamide.

5. The composition according to claim 1, wherein the compound of formula (I) is Rufinamide, and the compound of formula (II) is Lamotrigine.

6. The composition according to claim 1, wherein the composition comprises a pharmaceutically acceptable adjuvant, diluent, and/or carrier.

7. The composition according to claim 1, wherein the composition is in the form of a tablet.

8. A single oral dosage form comprising
a first formulation comprising a compound according to formula (I):

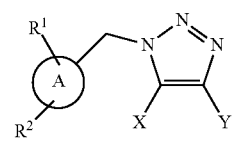

(I)

wherein,
A is an aryl that is a phenyl ring,
$R^1$ and $R^2$ are each a halogen that is a fluorine,
X is a hydrogen, and
Y is a carboxamide that is —$CONH_2$,
and
a second formulation comprising a compound according to formula (II)

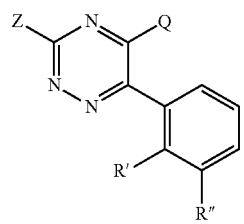

(II)

wherein,

Z and Q are each a $NH_2$, and

R' and R" are each a halogen that is a chlorine; and wherein a molar ratio of the compound according to formula (I) and the compound according to formula (II) is in a range from 7:0.5 to 3.1:1.

9. The single oral dosage form according to claim 8, wherein the compound of formula (I) is Rufinamide.

10. The single oral dosage form according to claim 8, wherein the compound of formula (I) is Rufinamide, and the compound of formula (II) is Lamotrigine.

11. The single oral dosage form according to claim 8, wherein the single oral dosage form comprises a pharmaceutically acceptable adjuvant, diluent, and/or carrier.

12. The single oral dosage form according to claim 10, wherein the single oral dosage form is in the form of a tablet, wherein the single oral dosage form comprises a pharmaceutically acceptable adjuvant, diluent, and/or carrier.

13. The composition according to claim 1, wherein the compound according to formula (I) is Rufinamide, the compound according to formula (II) is Lamotrigine, and the molar ratio of the compound according to formula (I) and the compound according to formula (II) is 7:0.5 or 3.1:1.

14. The single oral dosage form according to claim 8, wherein the compound according to formula (I) is Rufinamide, the compound according to formula (II) is Lamotrigine, and the molar ratio of the compound according to formula (I) and the compound according to formula (II) is 7:0.5 or 3.1:1.

15. A method for the treatment of myotonia and/or the treatment or alleviation of symptoms associated with myotonia, comprising administering to a subject in need thereof the single oral dosage form according to claim 8.

* * * * *